(12) United States Patent
Charles

(10) Patent No.: US 10,646,375 B2
(45) Date of Patent: May 12, 2020

(54) SYSTEMS AND METHODS FOR PRESSURE-DRIVEN TOOL ACTUATION

(71) Applicant: Novartis AG, Basel (CH)

(72) Inventor: Steven T. Charles, Memphis, TN (US)

(73) Assignee: Alcon Inc., Rue Louis-D' Affrey ( * ) Notice: Subject to any disclaimer, the term of this patent is extended or adjusted under 35 U.S.C. 154(b) by 217 days.

(21) Appl. No.: 15/862,192

(22) Filed: Jan. 4, 2018

(65) Prior Publication Data
US 2018/0193192 A1    Jul. 12, 2018

Related U.S. Application Data

(60) Provisional application No. 62/445,349, filed on Jan. 12, 2017.

(51) Int. Cl.
| | | |
|---|---|---|
| *A61F 9/007* | (2006.01) | |
| *A61B 17/3201* | (2006.01) | |
| *G05D 16/20* | (2006.01) | |
| *A61B 17/00* | (2006.01) | |
| *A61B 17/29* | (2006.01) | |
| *A61B 17/30* | (2006.01) | |

(52) U.S. Cl.
CPC ...... *A61F 9/00763* (2013.01); *A61F 9/00736* (2013.01); *A61B 17/3201* (2013.01); *A61B 2017/00225* (2013.01); *A61B 2017/00539* (2013.01); *A61B 2017/2918* (2013.01); *A61B 2017/305* (2013.01); *G05D 16/2006* (2013.01)

(58) Field of Classification Search
CPC .......................................... A61B 2017/00539; A61B 2017/00535; A61B 17/3203; A61F 9/00736; A61F 9/00754; A61F 9/00763
See application file for complete search history.

(56) References Cited

U.S. PATENT DOCUMENTS

| | | | | |
|---|---|---|---|---|
| 5,024,652 | A | * | 6/1991 | Dumenek ........... A61F 9/00763 604/22 |
| 8,312,800 | B2 | | 11/2012 | Turner et al. |
| 10,231,870 | B2 | * | 3/2019 | Clauson ............. A61F 9/00763 |
| 2008/0142093 | A1 | | 6/2008 | Turner et al. |
| 2009/0030436 | A1 | | 1/2009 | Charles |
| 2019/0025492 | A1 | * | 1/2019 | Bhagavatula ........ G02B 6/2552 |

OTHER PUBLICATIONS

Alcon. (2012). Constellation RFID Illumination Probes & Accessories [Catalog].
Grieshaber. (2011). Single-Use Instruments [Brochure].
Peyman, Gholam A., Miniaturization of the vitrophage: vitrectomy instrument, Can. J. Ophthalmol, vol. 15, Jan. 1980, pp. 49-50.

* cited by examiner

*Primary Examiner* — Sarah A Simpson

(57) ABSTRACT

The present disclosure describes systems and methods for pressure-driven micro-surgical tool actuation. The systems and methods may encompass the use of a remote handle held by a first hand of a user as well as a surgical tool located in the eye of a patient. A primary actuator may be included in remote handle and operable to be actuated by a mechanical force exerted on the handle. Actuating the primary actuator pressurizes a fluid within a length of tubing. The pressurized fluid may be transmitted to a dynamic tool held by a second hand of the user, where the pressurized fluid may be used to actuate a subordinate actuator. Actuation of the subordinate actuator may actuate a dynamic component of the dynamic tool.

18 Claims, 5 Drawing Sheets

SYSTEMS AND METHODS FOR PRESSURE-DRIVEN TOOL ACTUATION

TECHNICAL FIELD

The present disclosure relates to ophthalmic surgery and surgical equipment, and more specifically, to pressure-driven micro-surgical tool actuation in ophthalmic surgery.

BACKGROUND

Ophthalmic surgery is performed on the eye to save and improve the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in precision or accuracy of surgical techniques can make a tremendous difference in the patient's vision after the surgery.

In certain ophthalmic surgeries, interior portions of the eye are cut, grasped, or removed using miniaturized instruments, often referred to as micro-surgical tools. Such tools may contain mechanically actuated components that act upon the eye. For instance, micro-surgical tools may include forceps, shears, and scissors. Precise positioning of these tools allows their accurate use and improves patient outcomes, but precise positioning can be difficult to maintain while manually actuating the tools.

SUMMARY

The present disclosure provides a system for pressure-driven tool actuation. The system includes a remote handle operable to be held by a first hand of a user. The remote handle includes a first end operable to be inserted in an eye and a primary actuator operable to be actuated by a mechanical force exerted on the remote handle. The system further includes a length of tubing containing a fluid and connected to the remote handle such that the primary actuator is operable to apply pressure to the fluid in the length of tubing when the primary actuator is actuated. The fluid in the length of tubing is operable to transmit the pressure through the fluid. The system also includes a dynamic tool operable to be held by a second hand of the user. The dynamic tool includes a dynamic component operable to be inserted in the eye and a subordinate actuator connected to the length of tubing such that pressure transmitted through the fluid actuates the subordinate actuator. The subordinate actuator is operable to actuate the dynamic component in the eye.

The system may further include the following additional features, which may be used in any combinations with one another unless clearly mutually exclusive. The primary actuator may include a plurality of actuation levers situated around a circumference of the remote handle to define a semi-circular bearing surface. The mechanical force exerted on the handle may be a radial force about the circumference that acts upon at least a portion of the plurality of actuation levers. The remote handle may include two semi-circular shaped elongated housing parts surrounding a push-pull rod mechanism. The mechanical force exerted on the remote handle may be a radial force exerted about a circumference of the remote handle on the semi-circular shaped elongated housing parts. The remote handle may include a lever operable to apply pressure to an internal spring. The spring may be operable to apply pressure to the fluid in the length of tubing. The mechanical force exerted on the remote handle may be pressure on the lever. The primary actuator may include a pin and return spring actuator, a piston and cylinder actuator, a reciprocating piston actuator, a push-pull rod actuator, a diaphragm actuator, or a bellows actuator. The first end of the remote handle may include a static tool; the first end of the remote handle may include an endoilluminator. The first end of the remote handle may include moving parts that are not actuated by the primary actuator or the subordinate actuator. The length of tubing may be less than one meter long. The fluid may include air or a liquid. The subordinate actuator may include a pin and return spring actuator, a piston and cylinder actuator, a reciprocating piston actuator, a push-pull rod actuator, a diaphragm actuator, or a bellows actuator. The dynamic tool may also include a sliding sleeve. Actuation of the subordinate actuator may cause the sliding sleeve to slide over at least a portion of the dynamic component to cause actuation thereof. The subordinate actuator may also include a push-pull rod mechanism. The push-pull rod mechanism may include a sliding ring such that actuation of the subordinate actuator displaces the sliding ring. The dynamic component may include scissors, forceps, or shears. The dynamic tool may be removable.

The present disclosure further provides a method for pressure-driven tool actuation. The method includes applying pressure to a fluid in a length of tubing using a primary actuator in a remote handle in response to a mechanical force applied to the primary actuator by a first hand of a user; transmitting the pressure via the fluid to a dynamic tool; actuating a subordinate actuator in the dynamic tool in response to the transmitted pressure; and actuating a dynamic component of the dynamic tool in an eye in response to actuating the subordinate actuator, in which the dynamic tool is held by a second hand of the user.

The method may further include applying less pressure to the fluid in the length of tubing in response to a decrease or cessation of the mechanical force applied to the primary actuator; reducing or eliminating the fluid pressure transmitted to the dynamic tool in response to the decrease or elimination of the mechanical force applied to the primary actuator; diminishing or ceasing actuation of the subordinate actuator in response to the reduction or elimination of the applied fluid pressure; and diminishing or ceasing actuation of the dynamic component in response to the diminished or ceased actuation of the subordinate actuator.

Any of the above systems may be operated using any of the above methods and any of the above methods may be applied to any of the above systems.

BRIEF DESCRIPTION OF THE DRAWINGS

For a more complete understanding of the present disclosure and the associated features and advantages described herein, reference is now made to the following description, taken in conjunction with the accompanying drawings, which are not to scale, in which like numerals refer to like features, and in which.

Figure 2:
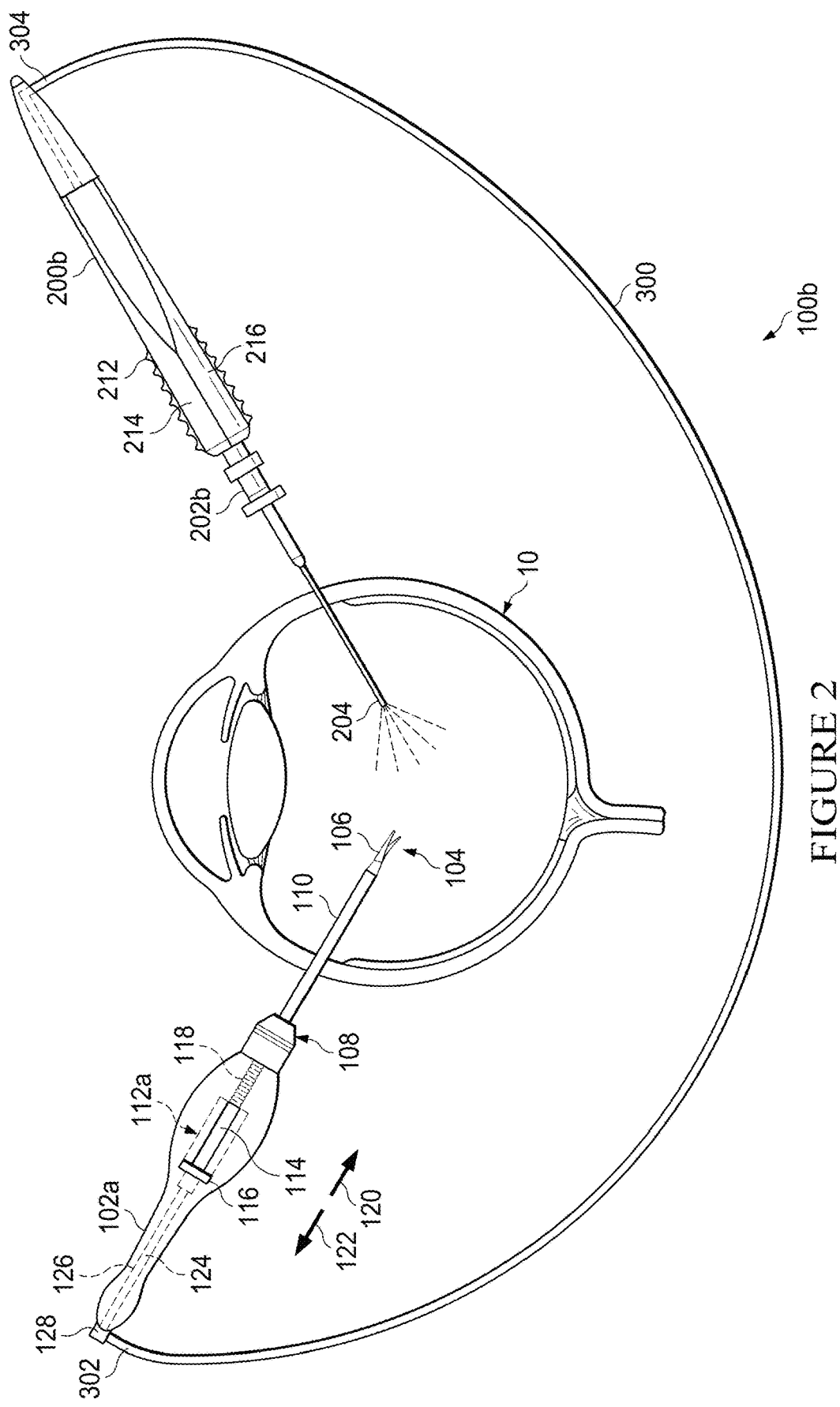
FIG. 2 is a perspective view of an example system for pressure-driven micro-surgical tool actuation with a squeeze handle similar to that of a GRIESHABER® RENAISSANCE® NG or GRIESHABER® RENAISSANCE®
Figure 3:
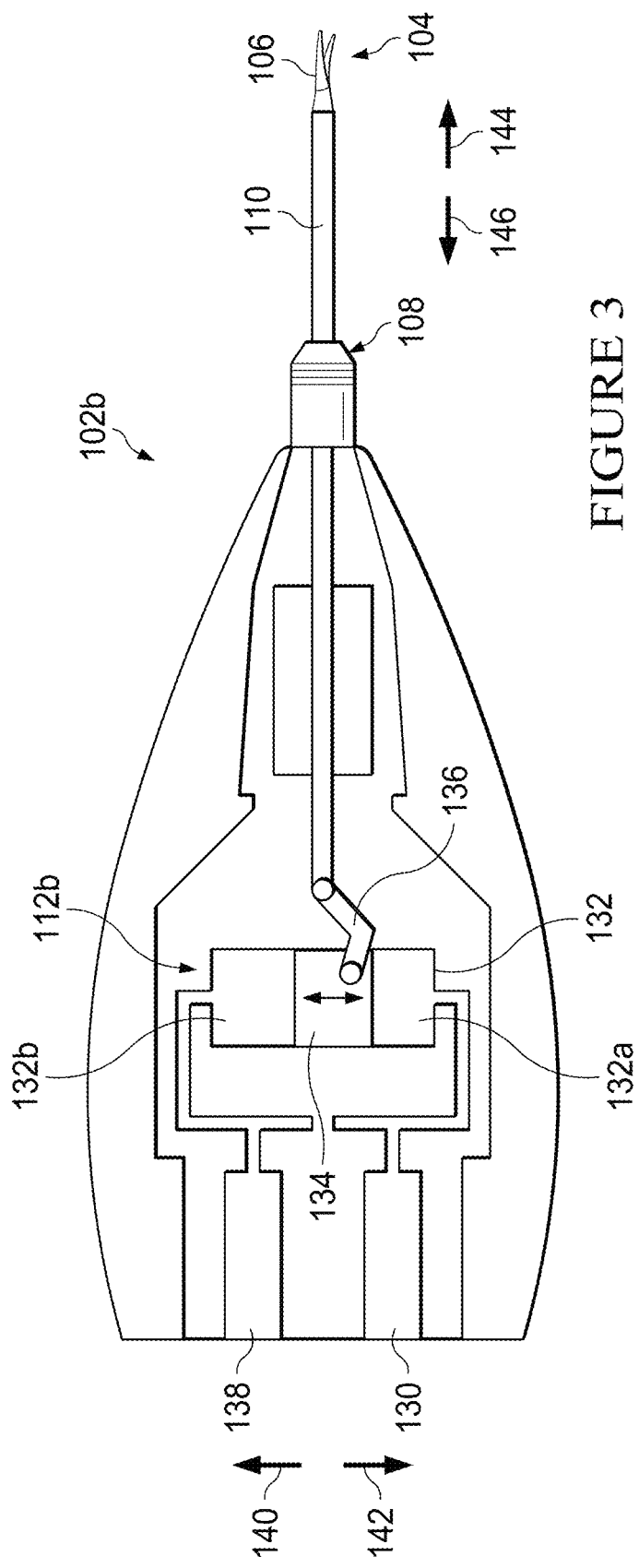
Figure 4:
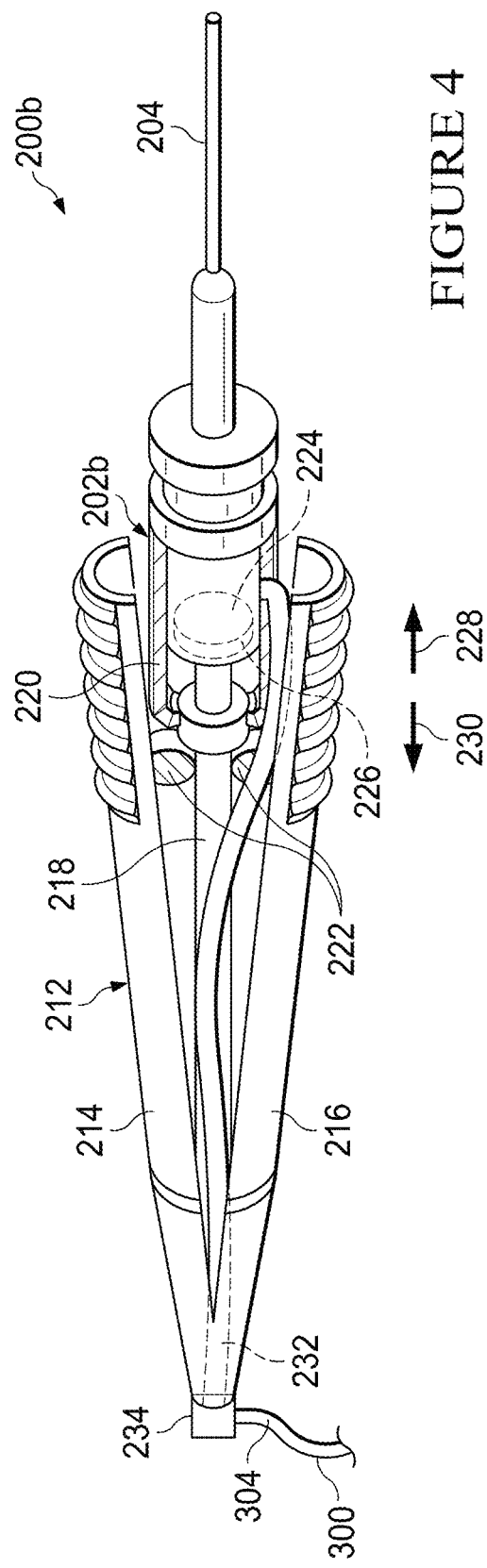
Figure 5:
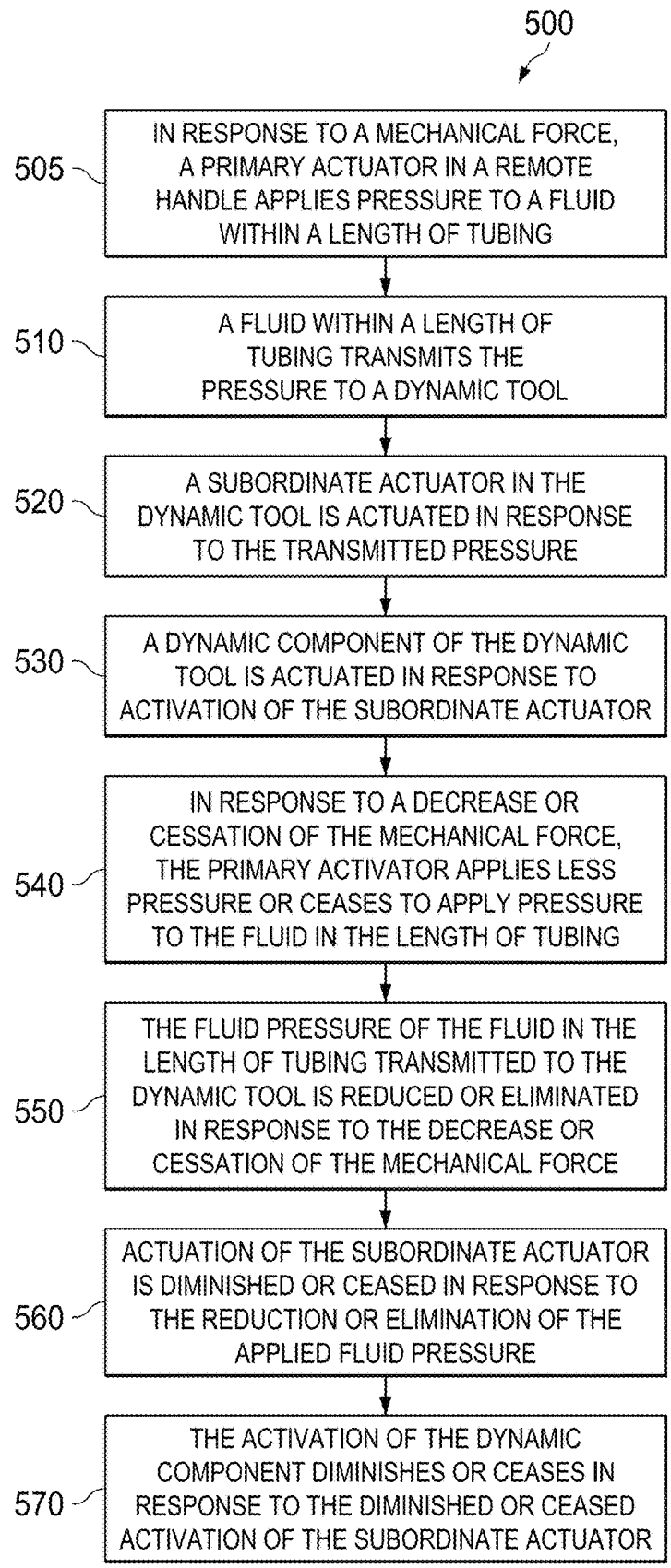

Advanced Handle both of which are produced by Alcon Laboratories, Inc., located at 6201 South Freeway, Fort Worth, Tex. 76134;

FIG. 3 is a schematic diagram of an example dynamic tool containing a subordinate actuator that has a reciprocating piston;

FIG. 4 is a schematic representation of an example primary actuator in a squeeze handle of the system of FIG. 2; and FIG. 5 is a flowchart of an example method for pressure-driven micro-surgical tool actuation.

DETAILED DESCRIPTION

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

The disclosed systems and methods for pressure-driven micro-surgical tool actuation may improve precise positioning of micro-surgical tools, particularly those with dynamic components located in the eye, by allowing one hand to make a motion that actuates those dynamic components in the eye while the other hand holds and positions the dynamic tool containing those dynamic components in the tool tip. This avoids or greatly reduces inadvertent tremor or position error of tool tip that sometimes occurs when using tools in which the same hand that holds and positions the dynamic tool also makes a motion that actuates its dynamic components. This inadvertent tremor or position error may often result from coupled actuation and positioning, hand fatigue, intention tremor, and other inadvertent hand movements. Using a system or method of the present disclosure, even if actuation effects, hand fatigue, and other inadvertent hand movements occur as a result of the motion that actuates the tool's dynamic components, they affect the hand that is not holding and positioning the tool tip, so negative effects, e.g., inadvertent tremor or position error of the tool tip containing the dynamic components, are avoided or minimized. In addition, systems and methods of the present disclosure may minimize and avoid negative effects of coupled actuation and tool tip positioning while still providing tactile feedback of the force applied to actuate the dynamic components. Such tactile feedback is simply switched to the hand not positioning the tool tip.

The disclosed systems and methods also avoid or greatly reduce the inadvertent tremor or position error of the tool tip in a dynamic tool that sometimes occurs when a foot, rather than a hand, makes the motion that actuates the micro-surgical tool's dynamic components. The user is typically seated during ophthalmic surgery, and foot movement is applied to press a foot pedal, for example, which causes actuation of the dynamic components. However, movement of the foot may cause movement of the user's entire leg, which tends to cause the user's entire body to shift. The systems and methods of the present disclosure, by allowing the motion that actuates the dynamic components to be performed by a hand, avoids body shifting or other movements that may happen when the user moves a foot. In addition, by allowing the user to control actuation with a hand instead of a foot, reaction time is improved and the frequency of actuation may be increased because hands can typically make more frequent movements than feet. Furthermore, because a hand instead of a foot is used to actuate the dynamic components, tactile feedback of the force applied to actuate the dynamic components is provided.

Systems of the present disclosure typically include a dynamic tool for use in one hand and a remote handle for use in the other hand. The dynamic tool and remote handle are connected via a length of tubing that is filled with a fluid that transmits pressure from the remote handle to the dynamic tool. Example systems and components are described in greater detail in FIGS. 1-4. However, aspects of these systems and components may be combined with one another and with systems and components otherwise described herein, but not illustrated in the figures.

Figure 1:
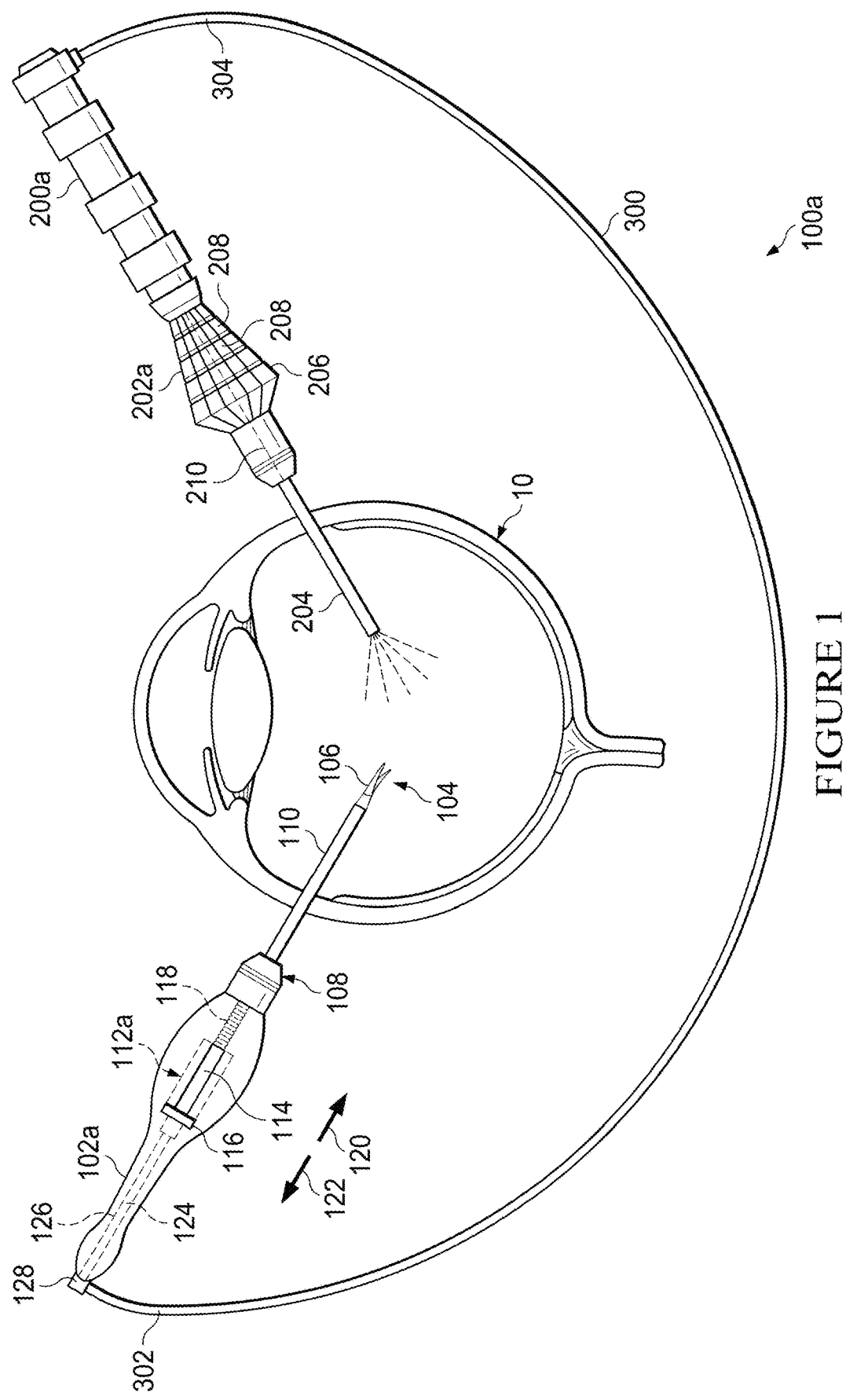
FIG. 1 is a perspective view of an example system for pressure-driven micro-surgical tool actuation with a basket handle similar to that of a GRIESHABER REVOLUTION® DSP handle produced by Alcon Laboratories, Inc., located at 6201 South Freeway, Fort Worth, Tex. 76134.

FIGS. 1 and 2 illustrate two systems for pressure-driven micro-surgical tool actuation systems 100*a* and 100*b*, respectively. The systems differ in the remote handle depicted, but otherwise contain similar components.

Referring to FIG. 1, a dynamic tool 102*a*, which is typically held in a user's dominant hand, includes a dynamic component 104 that is located in a patient's eye 10 (depicted to better illustrate how the systems may be used, but not a component of any system). The dynamic component 104 moves within the eye 10 when actuated. For instance, the dynamic component 104 may include scissors, such as the curved scissors 106 depicted in FIGS. 1 and 2, or vertical scissors. The dynamic component 104 may also include forceps, such as internal limiting membrane (ILM) forceps, end-grasping forceps, asymmetrical forceps, fiber optic forceps, and microtextured forceps, such as MAX GRIP® forceps also produced by Alcon Laboratories, Inc., located at 6201 South Freeway, Fort Worth, Tex. 76134. The dynamic component 104 may further include shears. However, the scope of the disclosure is not so limited. The dynamic component 104 is intended to encompass other types of mechanisms, tools, or instruments for use within a surgical procedure.

As depicted in FIGS. 1 and 2, the dynamic component 104 is located in or otherwise included as part of a tool tip 108. The tool tip 108 also includes a sliding sleeve 110. The sliding sleeve 110 may be pushed over the dynamic component 104, causing the dynamic component 104 to actuate. In the case of where the dynamic component 104 is a pair of scissor, such as the curved scissors 106, the sliding sleeve 110 engages the scissors, causing the scissors to close so as to perform a cutting action. When the sliding sleeve 110 retracts from the dynamic component 104, the dynamic component is returned to an unactuated condition. For example, in the case of the curved scissors 106, retraction of the sliding sleeve 110 cause the curved scissors 106 to open. Actuating mechanisms other than a sliding sleeve 110 for actuating the dynamic component 104 may also be employed. Typically, a type of actuating mechanism used may depend on the type of actuator contained in dynamic tool 102*a*. Thus, other mechanisms for compressing, closing, opening, or otherwise actuating the dynamic component 104 may be used in the dynamic tool 102*a*. For instance, a push-pull rod with a sliding ring directly or indirectly coupled to the second actuator and the dynamic component may be used instead of a sliding sleeve.

The tool tip 108 and any components thereof, such as the sliding sleeve 110 and the dynamic component 104, may be integrally formed with the dynamic tool 102a. In other implementations, the tool tip 108 and the associated components thereof may be removable and even replaceable with respect to the dynamic tool 102a.

In some implementations, the tool tip 108 and/or other portions thereof, such as the portions of the tool tip 108 inserted into the eye 10, may have a gauge size of 20 gauge, 23 gauge, 25 gauge, or 27 gauge. However, the scope of the disclosure is not so limited. Rather, the size of the tool tip 108 and/or any component thereof may have any desired size.

As illustrated in FIGS. 1 and 2, the system 110a also includes a subordinate actuator 112a is operable to actuate the dynamic component 104. The subordinate actuator 112a may include any type of actuator that may be driven by pressure transmitted through a fluid. For example, in some instances, the subordinate actuator 112a may include a pin and a return spring actuator; a piston and cylinder actuator; a reciprocating piston actuator; a push pull rod actuator; a diaphragm actuator; a bellows actuator; an actuator that combines one or more of the above-referenced actuators; or any other type of actuator. In some implementations, in order to further reduce inadvertent tremor or position error of the tool tip, the actuator may gradually respond to force rather than make an abrupt movement.

As illustrated in FIGS. 1 and 2, the subordinate actuator 112a includes 112a includes a pin 114 and a return spring 118. The pin 114 includes a head 116. In the illustrated examples, the head 116 is enlarged in comparison to the remainder of the pin 114. The subordinate actuator 112a receives an actuation force in the form of a fluid pressure that is transmitted through a fluid contained within a length of tubing 300. The fluid pressure transmitted through fluid contained in the tubing 300 may be provided by a remote handle, such as remote handle 200a or remote handle 200b discussed in more detail below. The fluid pressure acts on the head 116 and, when the resulting force is sufficient to overcome a biasing force of the spring 118, the pin 114 is displaced in the direction of arrow 120 along a longitudinal axis of the dynamic tool 102b. As a result, the pin 114 compresses the spring 118 and also applies a mechanical force to the sliding sleeve 110 sufficient to cause the sliding sleeve 110 to move in a direction towards the dynamic component 104. In the examples shown in FIGS. 1 and 2, the sliding sleeve 110 actuates the dynamic component by sliding over the dynamic component 104, causing the dynamic component 104 to close. Thus, in the case of the curved scissors 106, the sliding sleeve 110 slides over the curved scissors 106 causing the curved scissors 106 to close and perform a cutting action. When fluid pressure transmitted through the fluid in the tubing 300 is reduced such that force applied to pin 114 is no longer sufficient to overcome the biasing force imparted by compression of the spring 118, the spring 118 displaces the pin 114 in the direction of arrow 122, which, in turn, retracts the sliding sleeve 110 and returns the dynamic component 104 to an unactuated position.

A first end 302 of the length of tubing 300 may be sealingly connected to a conduit 124 of the dynamic tool 102a via a connector 128. The connector 128 may prevent fluid from leaking during operation of the dynamic tool 102a. In some implementations, the conduit 124 may be internal to the dynamic tool 102a. In other implementations, the conduit 124 may be disposed, in whole or in part, external to the dynamic tool 102a. In some implementations, the conduit 124 may be, in whole or in part, in the form of a length of rigid or flexible tubing. In the example shown in FIGS. 1 and 2, the conduit 124 is fluidly connected to the tubing 300 via the connector 128. In other implementations, the fluid within the tubing 300 may be separated from a passage 126 formed by the conduit 124. For example, in some implementations, flexible diaphragms may be used to separate fluid in the conduit 124 from fluid in the tubing 300 while still allowing pressure to be transmitted. A flexible diaphragm used to isolate the fluid within the tubing 300 from the passage 126 may be disposed in a connector used to join the tubing 300 to the conduit 124.

FIG. 3 illustrates another example dynamic tool 102b. In some implementations, this dynamic tool 102b may be used in place of dynamic tool 102a in the systems 100a and 100b illustrated in FIGS. 1 and 2, respectively. The dynamic tool 102b includes a subordinate actuator 112b, which is in the form of a reciprocating piston actuator. The subordinate actuator 112b includes a piston 134, movable within a piston housing 132, and a pivot arm 136. The pivot arm 136 may be pivotably connected to the piston 134 and to a sliding sleeve 110.

Pressure transmitted through fluid in tubing, such as tubing 300 shown in FIGS. 1 and 2, is transmitted through the subordinate actuator 112b and results in an alternating motion of a piston 134. When a pressure within the tubing is generated by a remote handle, such as the remote handle 200a or remote handle 200b, a fluid pressure may be generated within a fluid disposed within the dynamic tool 102b and be alternatingly sent to opposite sides of the piston 134. For example, fluid pressure generated within the fluid contained within the dynamic tool 102b may first be sent, via a first port 130, to a first side 132a of a piston housing 132. This fluid pressure may cause the piston 134 to be displaced in the direction of arrow 140. This displacement of piston 134 in the direction of arrow 140 causes a corresponding movement of attached pivot arm 136, which may be pivotably connected to the piston 134 and to a sliding sleeve 110. As the piston 134 is moved in the direction of arrow 140, the pivot arm 136 first pushes sliding sleeve 110 in the direction of arrow 144, causing the dynamic component 104 to actuate. The sliding sleeve 110 reaches a maximum amount of extension in the direction of arrow 144 when the piston 134 is approximately in a center position within the piston housing 132. As the piston continues 134 towards the second side 132a of the piston housing 132, movement of the sliding sleeve 110 reverses, and the sliding sleeve 110 begins to move in the direction of arrow 146.

The piston 134 behaves similarly when fluid pressure is removed from the first port 130 and applied to a second port 138. In such an occurrence, with the piston 134 located in the second side 132b, the piston 134 moves from in the direction of arrow 142, causing the sliding sleeve 110 to initially move in the direction of arrow 144. As the piston 134 passes through approximately the midpoint of the piston housing 132, the sliding sleeve 110 is reversed as a result of the pivot arm 136, and the sliding sleeve 110 begins moving in the direction of arrow 146. Thus, for each stroke of the piston 134 from the first side 132a of the piston housing 132 to the second side 132b of the piston housing 132 or vice versa, the sliding sleeve 110 reciprocates in opposing directions represented by arrows 144 and 146. In the illustrated example, the curved scissors 106 are actuated by sliding over the curved scissors 106 and causing the curved scissors 106 to close and open.

Reversal of the application of fluid pressure from the first port 130 (and, hence the first side 132a of the piston housing 132) to the second port 138 (and, hence, the second side 132b of the piston housing 132) may be accomplished by a valve controlled by a control signal. In some implementations, the control signal may be an electrical signal, a pneumatic signal, a hydraulic signal, or any other type of signal operable to cause the generated fluid pressure within the dynamic tool 102b to be directed to the second side 132b of the piston housing 132. The control signal may be provided by a processor contained within a surgical console, for example. In some implementations, the control signal may be manually supplied by a user or provided by an external control device.

In response to the control signal, the generated fluid pressure within the dynamic tool 102b is may be directed, via the second port 138, to the second side 132b of the piston housing 132. As explained above, this reversal of fluid pressure application from the first side 132a to the second side 132b of the piston housing 132 causes a reciprocation of the sliding sleeve 110 and corresponding actuation of the dynamic component 104. In this instance, reciprocation of the sliding sleeve 110 causes the curved scissors 106 to close and open, thereby performing a cutting action.

Fluid pressure within the dynamic tool 102b may be redirected back to the first port 130 in response to another control signal. As explained above, the control signal may be an electrical signal, a pneumatic signal, a hydraulic signal, or any other type of signal operable to cause the generated fluid pressure within the dynamic tool 102b to be redirected back to the first side 132a of the piston housing 132. In some implementations, the control signal may be generated by manually supplied by a user or provided by an external control device.

The direction of fluid pressure back and forth between the first side 132a of the piston housing 132 and the second side 132b of the piston housing 132 allows for repeated actuation and de-actuation of the dynamic component 104, e.g., opening and closing of the curved scissors 106 shown in FIG. 3, whenever pressure is transmitted through the fluid in tubing 300. That is, repeated actuation and de-actuation of the dynamic component 104 (as a result of repeated oscillation of the sliding sleeve 110 in the illustrated example of FIG. 3) may continue continuously so long as fluid pressure from the tubing, e.g., tubing 300, is maintained. Consequently, in some implementations, maintained transmittal of fluid pressure through the tubing 300 to the subordinate actuator 112b results in continuous cycles of actuation and de-actuation of the dynamic component 104. Once transmittal of the fluid pressure through the tubing 300 is removed, actuation and de-actuation of the dynamic component 104 is stopped.

In some instances, the control signal that directs the fluid pressure in the dynamic tool 102b to the first port 130 and the first side 132a of the piston housing 132 or to the second port 138 and the second side 132b of the piston housing 132 may be manually supplied by the user. In some implementations, the control signal manually supplied by the user may be supplied from a component other than a remote handle, such as remote handle 200a or 200b. In some implementations, the control signal may be provided by an external control device, such as a processor, and the signal may be in the form of an electrical signal, a pneumatic signal, a hydraulic signal, or any other type of signal. As explained above, a processor operable to generate the control signals may be included in a surgical console. Such a surgical console may be used to control various aspects of a surgical procedure. Example surgical consoles may include the Constellation® Vision System, the Infiniti® Vision System, or the Centurion® Vision System, each of which is produced by Alcon Laboratories, Inc., located at 6201 South Freeway, Fort Worth, Tex. 76134.

Although not illustrated, a pressure-driven micro-surgical tool actuation system may include a dynamic tool different from the dynamic tools 102a or 102b. In some implementations, the alternative dynamic tool may contain an alternative subordinate actuator different from the subordinate actuators 112a or 112b. The alternative subordinate actuator may be any actuator that actuates dynamic component 104 in response to pressure transmitted by the fluid in tubing 300. In some implementations, the alternative subordinate actuator may be, without limitation, a push-pull rod actuator, similar to that illustrated in remote handle 200b (discussed in more detail below); a diaphragm actuator; a bellows actuator; actuators that combine one or more of these actuators; or any other type of desired actuator.

In some implementations, in order to further reduce inadvertent tremor or position error of the tool tip, the subordinate actuator 112a or 112b may gradually respond to force rather than make an abrupt movement. Abrupt movements may, for example, result when static friction is suddenly overcome.

FIGS. 1, 2, and 4 illustrate the example remote handles 200a and 200b. Generally, the remote handles 200a and 200b are typically held in the user's non-dominant hand. In any case, the remote handles 200a and 200b are held in a hand other than the hand holding the dynamic tool, such as dynamic handle 102a or 102b. The remote handles 200a and 200b include a primary actuator 202a and 202b, respectively. When the user applies mechanical force to the remote handle 200a or 200b that causes the primary actuator 202a or 202b to actuate, the primary actuator 202a or 202b applies pressure to a fluid in the tubing 300. That fluid pressure is transmitted to the subordinate actuator 112a or 112b. The subordinate actuator 112a or 112b is actuated in response to the received fluid pressure, which, in turn, actuates the dynamic components 104.

In some implementations, the remote handle 200a or 200b and the primary actuator 202a or 202b may be in a configuration similar to those conventionally used to actuate a micro-surgical tool in ophthalmic surgery. For example, in some implementations, the remote handle 200a or 200b may be similar to or utilize components presently used in micro-surgical tools. However, in the present disclosure, the primary actuator 202a or 202b may apply pressure to the fluid in the tubing 300 instead of directly mechanically actuating a micro-surgical tool.

In FIG. 1, the primary actuator 202a of the remote handle 200a may be in the form of an actuator handle 206 having a plurality of actuation levers 208. Thus, in some implementations, the remote handle 200a may be similar to the GRIESHABER REVOLUTION® handle, the GRIESHABER REVOLUTION® DSP handle, or the handles described in U.S. Pat. Nos. 6,482,198 and 6,488,695, both of which are incorporated by reference herein. For the example shown in FIG. 1, the actuator handle 206 is operated by squeezing the plurality of actuation levers 208, typically symmetrically, with respect to an axis 210 of the actuator handle. For instance the user may exert a radial force about the circumference of the actuator handle 206, which acts upon at least a portion of the plurality of actuation levers 208 that are situated around the circumference of the remote handle 200a and that define a semi-circular bearing surface. The primary actuator 202a then applies pressure to the fluid in tubing 300.

In FIG. 2, the remote handle 200b is a squeeze handle that may be similar to the GRIESHABER® RENAISSANCE® handle or the handles described in U.S. Pat. No. 6,908,476, which is incorporated herein by reference herein. The squeeze handle has two semicircular-shaped elongated housing parts 214 and 216 surrounding a push-pull rod mechanism 218 (illustrated in FIG. 4) that applies pressure via a primary actuator 202b to the fluid in the tubing 300 when a radial force is exerted on the semi-circular shaped elongated housing parts 214 and 216.

FIG. 4 illustrates an example of the remote handle 200b shown in FIG. 2. As illustrated in FIG. 4, the remote handle 200b includes a housing 212, formed at least in part from semicircular-shaped elongated housing parts 214 and 216. The semicircular-shaped elongated housing parts 214 and 216 surround push-pull rod mechanism 218 and are attached at an acute angle at an end cap 234. The semicircular-shaped elongated housing parts 214 and 216 may be biased in an extended configuration in which the semicircular-shaped elongated housing parts 214 and 216 are radially separated from the push-pull rod mechanism 218. The primary actuator 202b includes a closed housing 220 that is in fluid communication with tubing 300 via the end cap 234. When a user exerts a force onto the semicircular-shaped elongated housing parts 214 and 216, such as a radial force about the circumference of remote handle 200b, e.g., typically by squeezing the remote handle 200b, the semicircular-shaped elongated housing parts 214 and 216 are compressed radially inward into a retracted configuration, causing a sliding ring 222 to move along the push-pull rod mechanism 218. The sliding ring 222 is shown in cross-section in FIG. 4. As a result, the push-pull rod mechanism 218 pressurizes a fluid, such as a sterile liquid, contained within the closed housing 220 (also shown in cross-section in FIG. 4) by movement of a pin 224 in the direction of arrow 228. As shown, the pin 224 includes an enlarged head 226. The generated fluid pressure is transmitted through fluid contained in a tubing 232 and to a dynamic tool, such as the dynamic tools 102a and 102b, via a fluid contained in the tubing 300. All or part of the tubing 232 may be internal or external to the housing 212. An end of the tubing 232 is in fluid communication with the closed housing 220 such that pressure exerted by the enlarged heard 226 is transmitted to the fluid contained within the closed housing 220, through the tubing 232, and to the fluid contained in the tubing 300.

As explained above, the semicircular-shaped elongated housing parts 214 and 216 may be biased in the extended configuration. Thus, removal of the force from the semicircular-shaped elongated housing parts 214 and 216 causes the semicircular-shaped elongated housing parts 214 and 216 to return to the extended configuration, thus causing the pin 224 to move in the direction of arrow 230.

As shown, the internal tubing 232 is fluidly connected, via the end cap 234, to a second end 304 of the tubing 300. The remote handle 200b may also use connectors, such as flexible diaphragms, that separate fluid in the internal tubing 232 from fluid in the tubing 300, while still allowing pressure to be transmitted from one to the other.

The remote handle 200b is illustrated in FIG. 4 as also including a surgical tool 204 at an end of the remote handle 200b opposite end cap 234. The surgical tool 204 (shown as an endoilluminator in FIGS. 1 and 2) is operable to provide illumination, such as to tissues to the eye 10 to aid a medical professional during a surgical procedure. However, the scope of the disclosure is not so limited. That is, the remote handles described herein need not necessarily include an endoilluminator. Rather, in other instances, the remote handle 200b may include other types of surgical tools or devices for use in a surgical procedure.

Although not illustrated, pressure-driven micro-surgical tool actuation systems of the present disclosure may include a remote handle other than the remote handle 200a or 200b. One alternative remote handle may be a GRIESHABER SUTHERLAND NG handle produced by Alcon Laboratories, Inc., located at 6201 South Freeway, Fort Worth, Tex. 76134. Thus, in some implementations, an alternative remote handle may be similar to the handles described in U.S. Pat. No. 5,634,918, which is incorporated herein by reference. A SUTHERLAND NG handle contains a lever that a user may depress with a finger, typically the thumb or index finger. Depression of the lever applies pressure against an internal spring, and pressurizes a fluid. The fluid pressure may be applied to the fluid in a length of tubing, such as tubing 300 for example.

While the primary actuators 202a and 202b are described herein, the scope of the disclosure is not so limited. Rather, a primary actuator used in a remote handle may be any sort of actuator that generates a fluid pressure in response to a mechanical force applied, for example, by a hand motion, to the remote handle. For example, other primary actuators may be or include a pin and return spring actuator, similar to that illustrated in dynamic tool 102a; a piston and cylinder actuator; a reciprocating piston actuator, similar to that illustrated in the dynamic tool 102b; a diaphragm actuator; a bellows actuator; actuators that combine one or more of these actuators; or any other desired actuator.

In order to further reduce inadvertent tremor or position error of the tool tip, the primary actuator, such as primary actuators 202a or 202b, may gradually respond to an applied force rather than making an abrupt movement. Abrupt movements may, for example, result when static friction is suddenly overcome.

In implementations in which the remote handle 200a or 200b is similar to a conventional handle, the associated primary actuator 202a or 202b or other internal components may be modified such that the primary actuator applies pressure to a fluid in a length of tubing. While FIG. 4 illustrates an example conventional handle that has been modified in such a manner, other conventional handles may be modified in a similar manner to form a remote handle.

Remote handles, such as those r illustrated in FIGS. 1-2 and 4, may also include a surgical tool 204 (shown as an endoilluminator in FIGS. 1-2). The surgical tool 204 may be inserted in eye 10 during ophthalmic surgery. The surgical tool 204 may be one that is typically less sensitive to hand movement or for which inadvertent tremor or position error is less likely to result in a poorer surgical outcome as compared to the dynamic tool 102a or 102b and the associated dynamic component 104. For instance, the surgical tool 204 may lack moving parts located within eye 10, although the surgical tool 204, itself, may be moved within eye 10 during surgery. Examples of such surgical tools 204 may include an endoilluminator, as depicted in FIGS. 1-2; an aspirator; a pic; a blade; or other types of tools or instruments. In other implementations, the surgical tool 204 may contain moving parts. For example, in some instances, the surgical tool 204 may include moving parts that are not actuated by the primary actuator 202a or 202b or the subordinate actuator 112a or 112b. Examples of such surgical tools 204 include vitrectomy probes. The surgical tool 204 and any components thereof may be integrally formed with remote handle 200, or, in other instances, the components of the surgical tool 204 may be removable and even replaceable.

The tubing 300 may be sealingly connected to both the dynamic tool 102a or 102b and the remote handle 200a or 200b, so that pressure may be transmitted through the fluid contained within the tubing 300 in response to the actuation of the primary actuator 202a or 202b. In some instances, the sealing connection may be fluid-tight. Thus, in some implementations, the fluid is prevented from leaking out of the systems 100a and 100b, such as from the connections between the tubing 300 and the dynamic tool 102a or 102b and the remote handle 200a or 200b.

The tubing 300 may be made of a plastic, rubber, metal, or other material. Further, in some instances, the tubing 300 may be formed from a medical grade material. Additionally, the tubing 300 may have a diameter suitable to allow pressure to be transmitted therethrough.

In order to avoid decreases in pressure that occur as transmission distances increase, the length of the tubing 300 may be minimized. For instance, the tubing 300 may be less than one meter in length, less than 0.5 meters in length, or less than 0.3 meters in length. However, the length of the tubing 300 may be any desired length that still permits the transmission of pressure to cause actuation of a dynamic tool. The tubing 300 may be formed in discrete lengths. In other implementations, a length of the tubing 300 may be formed by cutting a continuous piece of tubing into a desired length, a standard length, or an otherwise specified length. Thus, in some instances, the length of the tubing 300 may be selected to provide an optimal size for different applications and/or conditions.

The tubing 300 and the connectors used to attach the tubing 300 to the dynamic tool 102a or 102b and the remote handle 200a or 200b may be similar to tubing and connectors conventionally used with foot-actuated ophthalmic surgery systems. In general, a short length of the tubing 300 is desirable, since the user's hands will typically be close to one another during an ophthalmic surgical procedure.

In some implementations, the fluid in tubing 300 may be air. However, at room temperature air is highly compressible, making pressure transmission less than optimal in some systems. Thus, in other implementations, the fluid within the tubing 300 may be a liquid. A liquid, such as a sterile, biologically inactive liquid, may be used. For example, the liquid may be a balanced salt solution, such as BSS® or BSS PLUS® produced by Alcon Laboratories, Inc., located at 6201 South Freeway, Fort Worth, Tex. 76134. However, other liquids may be used, e.g., water, other types of saline solutions, an oil, or other liquids. Being essentially incompressible, a liquid transmits pressure very well hydraulically.

Any components of the systems within the scope of the disclosure, such as, for example, systems 100a and 100b, may be removable or replaceable. For example, the remote handle, the surgical tool of the remote handle, the dynamic tool, the tool tip of the dynamic tool including the dynamic component, and/or the tubing may be replaceable. Replaceable components may be reusable or disposable. Some systems within the scope of the disclosure may contain a combination of disposable and reusable components.

FIG. 5 is a flowchart of an example method 500 for pressure-driven tool actuation. Method 500 may be particularly applicable to micro-surgical tool actuation. In some instances, the method 500 may be accomplished by one or more of the systems described herein, such as system 100a and 100b. Additionally, actions described above with respect to components of the systems encompassed by the present disclosure and as described herein may be performed in the method 500, even if not expressly described in connection with the flow chart.

At step 505, in response to a mechanical force, a primary actuator in a remote handle applies pressure to a fluid in a length of tubing. In some implementations, the mechanical force may be a motion made by a first hand of a user, such as a squeezing motion. Also, in some implementations, the user may hold the remote handle in the non-dominant hand and use the non-dominant hand to make the motion.

At step 510, a fluid within a length of tubing transmits the pressure to a dynamic tool.

At step 520, a subordinate actuator in the dynamic tool is actuated in response to the transmitted pressure.

At step 530, a dynamic component of the dynamic tool is actuated in response to actuation of the subordinate actuator. In some implementations, the dynamic component is located in a patient's eye. Actuating the dynamic tool may involve, for example, compressing, closing, or opening the dynamic tool. In some implementations, the dynamic tool may be held in a user's dominant hand. Because the mechanical force in step 505 is generated by a hand different than the one holding the dynamic tool, a tool tip of the dynamic tool may be positioned more precisely than if the same hand were applying the mechanical force were also holding the dynamic tool. Additionally, because a hand is still used to actuate the dynamic tool, tactile feedback of the mechanical force is realized.

At step 540, in response to a decrease or cessation of the mechanical force, the primary actuator applies less pressure or ceases to apply pressure to the fluid in the length of tubing. The fluid pressure of the fluid within the length of tubing may be reduced or eliminated by a decrease or cessation of the mechanical force.

At step 550, the fluid pressure of the fluid in the length of tubing transmitted to the dynamic tool is reduced or eliminated in response to the decrease or cessation of the mechanical force.

At step 560, actuation of the subordinate actuator is diminished or is ceased in response to the reduction or elimination of the applied fluid pressure.

In step 570, the actuation of the dynamic component diminishes or ceases in response to the diminished or ceased actuation of the subordinate actuator.

Although the method 500 illustrates an example method for pressure-driven tool actuation, particularly for micro-surgical applications, other methods for pressure-driven tool actuation may include fewer, additional, and or a different arrangement of operations. For example, although not depicted in FIG. 5, the method 500 may further include locating a surgical tool that is part of the remote handle in the eye.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A system for pressure-driven tool actuation comprising:
 a remote handle operable to be held by a first hand of a user and comprising:
  a first end operable to be inserted in an eye; and
  a primary actuator operable to be actuated by a mechanical force exerted on the remote handle;
 a length of tubing comprising a fluid and connected to the remote handle such that the primary actuator is operable to apply pressure to the fluid in the length of tubing when the primary actuator is actuated, the fluid in the length of tubing operable to transmit the pressure through the fluid; and a dynamic tool operable to be held by a second hand of the user and comprising:
   a dynamic component operable to be inserted in the eye; and
   a subordinate actuator connected to the length of tubing such that pressure transmitted through the fluid actuates the subordinate actuator, the subordinate actuator operable to actuate the dynamic component in the eye.

2. The system of claim 1, wherein the primary actuator comprises a plurality of actuation levers situated around a circumference of the remote handle to define a semi-circular bearing surface, and wherein the mechanical force exerted on the remote handle is a radial force about the circumference that acts upon at least a portion of the plurality of actuation levers.

3. The system of claim 1, wherein the remote handle comprises two semi-circular shaped elongated housing parts surrounding a push-pull rod mechanism, and wherein the mechanical force exerted on the remote handle is a radial force exerted about a circumference of the remote handle on the semi-circular shaped elongated housing parts.

4. The system of claim 1, wherein the remote handle comprises a lever operable to apply pressure to an internal spring, which is operable to apply pressure to the fluid in the length of tubing, and wherein the mechanical force exerted on the remote handle is pressure on the lever.

5. The system of claim 1, wherein the primary actuator comprises a pin and return spring actuator, a piston and cylinder actuator, a reciprocating piston actuator, a push-pull rod actuator, a diaphragm actuator, or a bellows actuator.

6. The system of claim 1, wherein the first end of the remote handle comprises a static surgical tool.

7. The system of claim 6, wherein the first end of the remote handle comprises an endoilluminator.

8. The system of claim 1, wherein the first end of the remote handle comprises moving parts that are not actuated by the primary actuator or the subordinate actuator.

9. The system of claim 1, wherein the length of tubing is less than one meter long.

10. The system of claim 1, wherein the fluid comprises air.

11. The system of claim 1, wherein the fluid comprises a liquid.

12. The system of claim 1, wherein the subordinate actuator comprises a pin and return spring actuator, a piston and cylinder actuator, a reciprocating piston actuator, a push-pull rod actuator, a diaphragm actuator, or a bellows actuator.

13. The system of claim 1, wherein the dynamic tool further comprises a sliding sleeve and wherein actuation of the subordinate actuator causes the sliding sleeve to slide over at least a portion of the dynamic component to cause actuation thereof.

14. The system of claim 1, wherein the subordinate actuator further comprises a push-pull mechanism that includes a sliding ring, wherein actuation of the subordinate actuator displaces the sliding ring.

15. The system of claim 1, wherein the dynamic component comprises scissors.

16. The system of claim 1, wherein the dynamic component comprises forceps.

17. The system of claim 1, wherein the dynamic component comprises shears.

18. The system of claim 1, wherein the dynamic component is removable.

* * * * *